United States Patent

Salama

[11] Patent Number: 5,306,226
[45] Date of Patent: Apr. 26, 1994

[54] URINARY CONTROL WITH INFLATABLE SEAL AND METHOD OF USING SAME

[76] Inventor: Fouad A. Salama, 3220 Valley Ridge Ct., West Des Moines, Iowa 50265

[21] Appl. No.: 61,770

[22] Filed: May 14, 1993

Related U.S. Application Data

[63] Continuation of Ser. No. 600,629, Oct. 22, 1990, abandoned, which is a continuation-in-part of Ser. No. 307,992, Feb. 9, 1989, Pat. No. 4,968,294.

[51] Int. Cl.⁵ ............................................. A61M 25/00
[52] U.S. Cl. ............................. 600/29; 128/DIG. 25; 604/96
[58] Field of Search ............... 600/29; 128/DIG. 25; 604/96, 103, 128, 247, 347, 349–353

[56] References Cited

U.S. PATENT DOCUMENTS

| | | |
|---|---|---|
| 274,447 | 3/1883 | Kennish . |
| 2,230,150 | 1/1941 | Winder .................... 604/96 |
| 2,547,758 | 4/1951 | Keeling ................... 604/174 |
| 2,690,595 | 10/1954 | Raiche .................... 604/96 |
| 3,394,705 | 7/1968 | Abramson ................ 604/280 |
| 3,459,175 | 8/1969 | Miller ..................... 604/96 |
| 3,463,141 | 8/1969 | Mozolf .................... 128/887 |
| 3,503,400 | 3/1970 | Osthagen et al. ........ 128/DIG. 25 |
| 3,631,857 | 1/1972 | Maddison ................ 604/349 |
| 3,707,146 | 12/1972 | Cook et al. .............. 604/96 |
| 3,707,957 | 1/1973 | Bucalo .................... 128/843 |
| 3,731,670 | 5/1973 | Loe . |
| 3,758,073 | 9/1973 | Schulte ................... 251/342 |
| 3,768,102 | 10/1973 | Kwan-Gett et al. . |
| 3,841,304 | 10/1974 | Jones ...................... 128/DIG. 25 |
| 3,977,408 | 8/1976 | Mackew . |
| 4,089,337 | 5/1978 | Kronner .................. 604/178 |
| 4,211,233 | 7/1980 | Lin ......................... 604/96 |
| 4,419,097 | 12/1983 | Rowland ................. 604/352 |
| 4,457,299 | 7/1984 | Cornwell . |
| 4,575,371 | 3/1986 | Nordquist et al. ....... 604/96 |
| 4,587,954 | 5/1986 | Haber . |
| 4,626,250 | 12/1986 | Schneider ................ 604/347 |
| 4,643,169 | 2/1987 | Koss et al. . |
| 4,710,169 | 12/1987 | Christopher ............. 604/104 |
| 4,810,247 | 3/1989 | Glassman ................ 604/171 |
| 4,813,935 | 3/1989 | Haber et al. ............. 604/103 |
| 4,820,270 | 4/1989 | Hardcastle et al. ...... 604/96 |
| 4,822,333 | 4/1989 | Lavarenne ............... 604/104 |
| 4,846,784 | 7/1989 | Haber . |
| 4,932,938 | 6/1990 | Goldberg ................. 604/247 |
| 4,946,449 | 8/1990 | Davis, Jr. ................ 128/DIG. 25 |
| 5,007,897 | 4/1991 | Kalb et al. ............... 604/96 |
| 5,030,199 | 7/1991 | Barwick et al. ......... 600/29 |

FOREIGN PATENT DOCUMENTS

| | | |
|---|---|---|
| 948947 | 6/1947 | Canada ................... 128/843 |
| 2600259 | 7/1976 | Fed. Rep. of Germany ... 128/DIG. 25 |
| 2818119 | 11/1979 | Fed. Rep. of Germany ........ 604/96 |
| 3421568 | 12/1985 | Fed. Rep. of Germany ... 128/DIG. 25 |
| 0268626 | 6/1989 | Fed. Rep. of Germany ........ 604/96 |
| 479468 | 3/1954 | Italy ....................... 604/96 |

OTHER PUBLICATIONS

C. R. Bard Inc., Catalog "Catheters and Urological Specialties" pp. B-10, B-11 ©1968.
American Cystoscope Makers, Inc., Advertisement in *Surgery, Gynecology, and Obstetrics*, p. 12, Feb. 1937.

*Primary Examiner*—Ralph Lewis
*Attorney, Agent, or Firm*—Zarley, McKee, Thomte, Voorhees & Sease

[57] ABSTRACT

A urine tube extends through a balloon which is inflatable in the neck of a bladder to form a seal around the urine tube. The balloon has a shape corresponding to the shape of the bladder chamber at the urethra orifice to facilitate establishing a seal. A valve is provided on the outlet end of the urine tube and an air tube extends along the substantial length of the urine tube into the balloon. A hypodermic syringe or the like may be inserted into the inlet end of the air tube for inflating the balloon. A hydrogel collar is positioned around the urine tube against the body at the outlet end of the urethra to hold the balloon in tight engagement with the bladder neck at the urethra orifice.

14 Claims, 2 Drawing Sheets

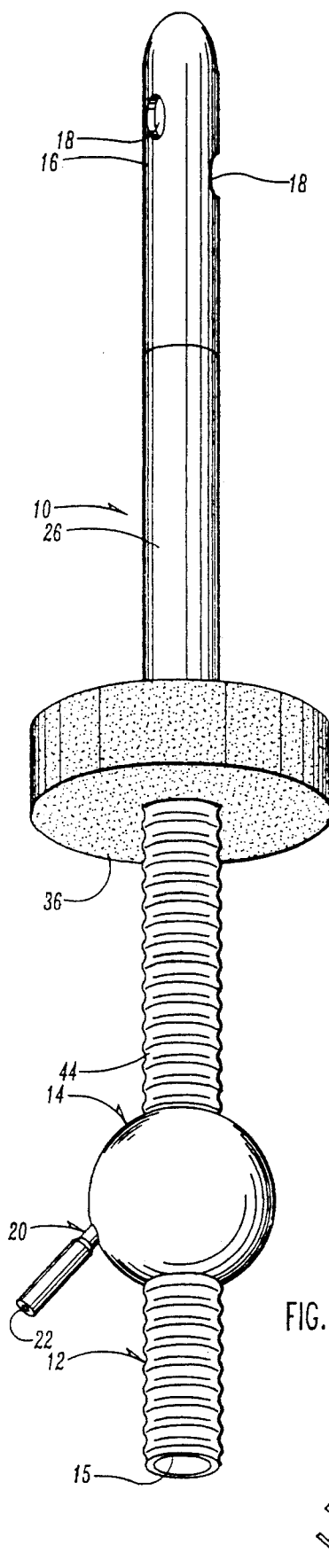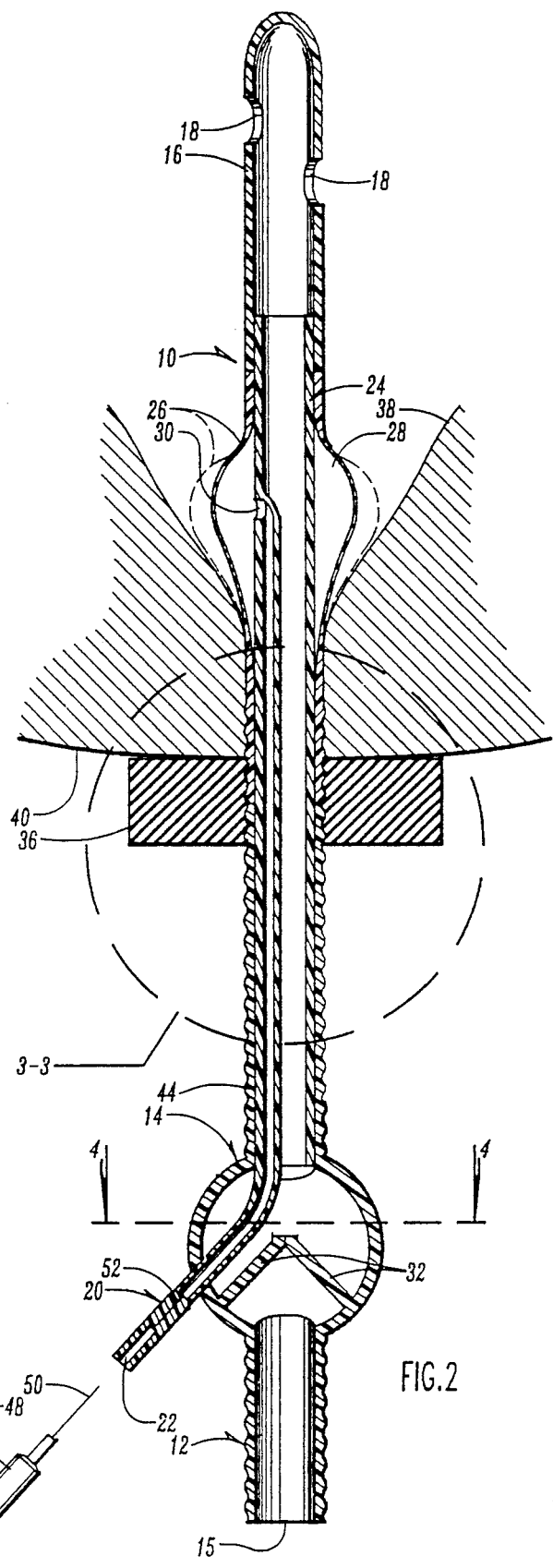

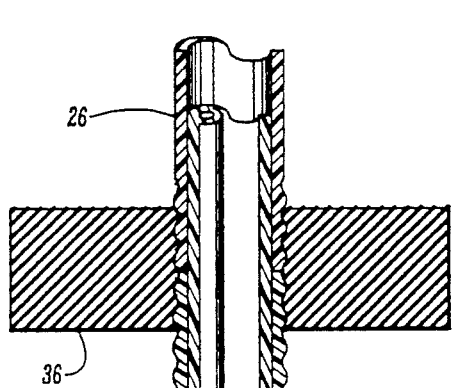
FIG.3
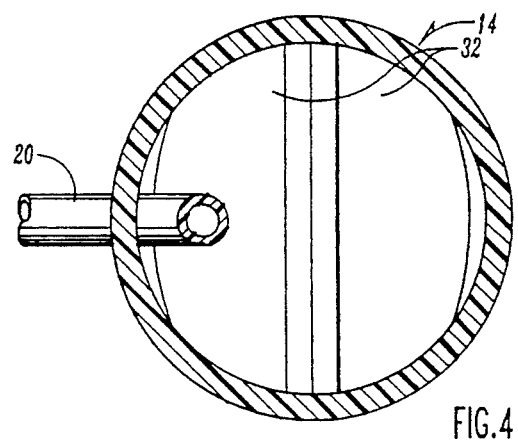
FIG.4
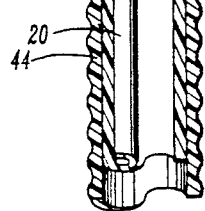
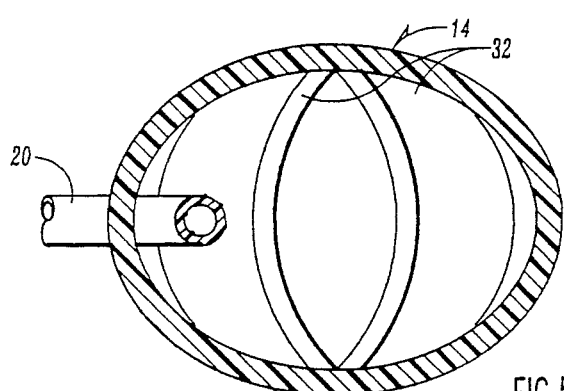
FIG.5
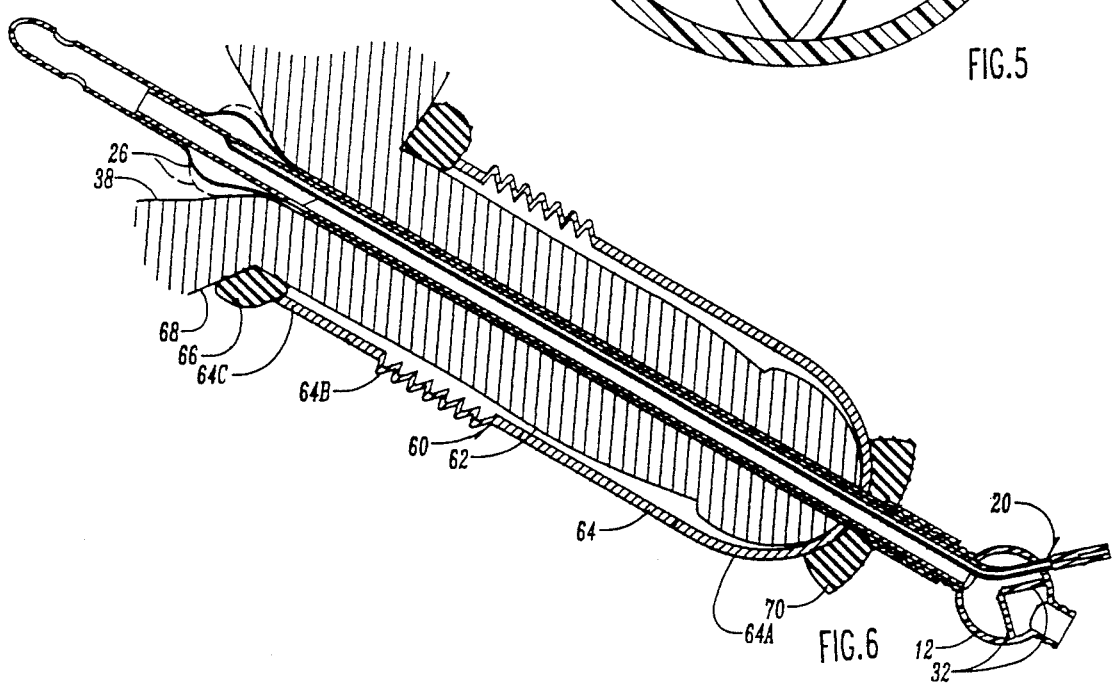
FIG.6

URINARY CONTROL WITH INFLATABLE SEAL AND METHOD OF USING SAME

BACKGROUND OF THE INVENTION

This is a continuation of application Ser. No. 07/600,629 filed Oct. 22, 1990 now abandoned which is a continuation-in-part of application Ser. No. 07/307,992 filed Feb. 9, 1989, URINARY CONTROL VALVE & METHOD OF USING SAME, now U.S. Pat. No. 4,968,294.

Incontinence is a problem for many people including older adults. Present day approaches to dealing with incontinence such as the Foley catheter often times causes urinary tract infection. A bag for urine is required and smell becomes a problem. The chances of infection are increased each time the bag is changed. The cost for the Foley catheters and bags is substantial. An inflatable conventional spherical balloon is used to keep the catheter in the bladder, but leakage around the catheter occurs and is a problem. It was not an object of this product to provide a seal around the catheter at the bladder orifice.

In my co-pending application I have disclosed a urethral valve positioned in the orifice of the urethra. In some instances, leakage may occur around the outside of the valve. What is needed is a simple inexpensive device for controlling urine flow in the urethra which is compatible to the body and will not cause discomfort, infection and pass urine only through operation of the valve rather than around the outside of the catheter.

SUMMARY OF THE INVENTION

A urinary tube extends into the urethra and continues into the bladder. An inflatable balloon having a lower end portion extending into the urethra has a shape corresponding to the shape of the inner wall surface of the bladder at the orifice, extends around the bladder end of the urinary tube and an air line extends through the urine tube to outside the urethra where it is adapted to be connected to an air pump for inflating the balloon to provide a plug seal in the urethra around the urinary tube in the neck and orifice of the bladder. A valve is provided in the urinary tube outside of the urethra.

An anchoring collar of hydrogel frictionally engages the exterior of the urinary tube and is positioned against the outer end of the urethra to hold the balloon lower end portion in tight sealing engagement in the urethra in the neck of the bladder.

The urinary control of this invention when used by a male includes the additional use of a support shell around the penis to stabilize the urinary tube which extends through the penis. The anchoring collar of hydrogel is positioned against the outer end of the support shell. The shell is one piece but includes a plurality of sections to allow for fitting the support shell to penises of different sizes. A collar of hydrogel is also placed between the inner end of the shell sections and the pubic bone base of the penis. An accordion type section is included to give the shell flexibility in accommodating penises of different lengths and to permit them to be disposed at varying angles to the body.

A hypodermic syringe or the like may function as an air pump when its needle is inserted into the air tube to inflate the balloon.

DESCRIPTION OF THE DRAWINGS

FIG. 1 is a fragmentary perspective view of the urinary control with inflatable seal.

FIG. 2 is a longitudinal cross-sectional view of the urinary control in the urethra of a female.

FIG. 3 is an enlarged cross-sectional view of the structure indicated by the line 3—3 in FIG. 2.

FIG. 4 is a cross-sectional view taken along line 4—4 in FIG. 2 showing the valve in a closed condition.

FIG. 5 is a view similar to FIG. 4 but showing the valve in an open condition.

FIG. 6 is a view similar to FIG. 2 but showing the urinary control in the urethra of a male.

DESCRIPTION OF THE PREFERRED EMBODIMENT

The urinary control of this invention is referred to generally by the reference numeral 10 as seen in FIG. 1 and includes a urine tube 12 in which a valve 14 is connected. The tube 12 has an outer outlet end 15 and an inner inlet end 16 with sidewall openings 18.

An air tube 20 extends into the valve body 14 and along the length of the tube 12 towards the inlet end 16. The air tube 20 has an inlet end 22 and an outlet end 24 positioned in a balloon 26 formed in part by the sidewalls of the urine tube 14. Balloon chamber 28 is provided. The air tube outlet end includes an opening 30 in chamber 28.

The valve body 14 includes a pair of oppositely disposed blade elements 32 normally closed. Pressure on the opposite sidewalls of the valve body 14 will cause the valve elements 32 to spread as seen in FIG. 5 and allow urine to flow toward the outlet end 14.

An anchoring collar means 36 of hydrogel is provided around the urine tube 12 outwardly of the balloon 26 and frictionally engages the outer surface of the urine tube 12 to hold the walls of the balloon 26 in tight sealing contact with the bladder orifice and neck 38 as seen in FIG. 2. The balloon 26 is shaped to correspond to the shape of the inner side walls of the bladder at the orifice to provide a seal around the catheter thereby preventing leakage. This shape is generally pear shape as seen in FIGS. 2 and 6, the balloon 26 when inflated includes an enlarged upper portion which merges into a downwardly extending reduced in size lower portion. In the female, the collar 36 presses against the body around the opening to the urethra. A sleeve 42 also extends around the urine tube 12 and may be adjusted tightly against the collar 36 to assist in holding the collar tight against the person's body at the outlet end of the urethra. Rounded serrations 44 are provided along the outside of the urine tube 12 and register with serrations on the inside face of the collar 36 and serve to hold the collar 36 in place in turn holding the balloon seal 26 in place thereby preventing leakage around the tube 12.

A hypodermic syringe 48 functions as an air pump and has a needle 50 which is inserted into the inlet end 22 of the air tube 20. The inlet end 22 has a passageway 52 normally closed except when opened by the needle 50 thereby allowing air to be introduced into the tube to fill the balloon 26 but when the needle 50 is removed the passageway is sealed preventing air from escaping and deflating the balloon.

When the urinary control of this invention is used on a male, a one piece support shell 60 is provided around the penis 62 and includes an outer section 64 having an outer end 64A being rounded to the curvature of the head of the penis. An accordion pleats section 64B interconnects the outer section 64 with a base section 64C. The base section 64C presses against a hydrogel collar 66 which presses against the base (pubic bone) 68 of the penis. A second hydrogel collar 70 is positioned against the outer end of the rounded section 64A to hold the urine tube 12 in place such that the lower portion of the balloon 26 when inflated is pressed against the bladder neck 38 and into the urethra. Among the properties of hydrogel is that it is soft and pliable but yet firm.

In use it is seen that the urine tube 12 will be inserted into the urethra of the male or female far enough that the of the balloon 26 will function as a retention means and the lower portion will be seated in the urethra at the neck 38 of the bladder and functions as a plug to prevent urine flow on the outside of the urine tube 12. Air is introduced into the air tube 20 through the use of a hypodermic syringe. A hydrogel collar is then positioned against the body at the outer end of the urethra to hold the balloon 26 in position to maintain the seal in the urethra the bladder neck 38. The balloon is inflated from the solid line position in FIG. 2 to the dash line inflated condition. When fully installed, no urine can leak around the urine tube 12 due to the seal the balloon 26 provides with the bladder neck 38. Urine can enter the openings 18 in the inlet end 16 of the urine tube 12 and pass into the valve 14 and upon actuation of the valve blades 32 by applying pressure to opposite sides of the valve 14, the valve will be open for drainage of the bladder through the outlet end 15.

The valve 14 and urine tube 12 are formed from elastomer silicone material of a 50 or 55 durometer from Dow Corning, Midland, Mich. Tubing of this material is flexible and longitudinally collapsible such that longitudinal compressive pressure applied to it will not unseat the balloon lower portion in the urethra at the neck and orifice of the bladder and cause leakage around the tubing. The balloon 26 may have a capacity of approximately 40 cc's.

I claim:

1. The method of controlling the urine flow in the urethra comprising the steps of,
   providing an inflation tube having an inflatable balloon at one end and an inlet at the opposite end, said balloon having a non spherical shape when inflated and a downwardly extending lower end portion,
   providing a urine tube operatively connected to the inflation tube with the urine tube extending through the balloon and having a valve to limit urine flow from the urine inlet tube end to the urine outlet tube end,
   inserting the urine tube, and inflation tube and balloon into the urethra and positioning the deflated balloon in the bladder with the lower end portion in the urethra at the neck and orifice of the bladder with the inlet end of the urine tube being in the bladder,
   inflating the balloon to provide a plug seal in the urethra at the neck and orifice of the bladder to prevent urine flow in the urethra on the outside around the urine tube, and
   operating the valve to allow flow of urine from the bladder through the urine tube to the urine tube outlet end.

2. The method of claim 1 and the step of providing an anchoring means on said urine tube and inflation tube at the outlet end of the urethra for maintaining the lower end portion of the balloon in the urethra.

3. The method of claim 2 and the further steps of positioning the anchoring means in operative engagement with the body at the outlet end of the urethra for seating the lower end portion in the urethra.

4. The method of claim 3 and the step of providing a support shell around the penis and extending the outlet end of the urine tube outwardly of the outer end of the support shell with the anchoring means being in engagement with the outer end of the support shell and the inner end of the support shell engaging the users body adjacent the penis to provide resistance in pulling the balloon tight.

5. The method of controlling the urine flow in the urethra comprising the steps of,
   providing an inflation tube having an inflatable balloon at one end and an inlet at the opposite end, said balloon when inflated having an enlarged, upper portion and a downwardly extending reduced in size lower end portion,
   providing a urine tube operatively connected to the inflation tube with the urine tube extending through the balloon,
   inserting the urine tube, and inflation tube and balloon into the urethra and positioning the deflated balloon in the bladder with the lower end portion in the urethra at the neck and orifice of the bladder with the inlet end of the urine tube being in the bladder,
   inflating the balloon whereby the upper portion retains the balloon in the bladder and the lower end portion functions as a plug seal in the urethra at the neck and orifice of the bladder to prevent urine flow in the urethra on the outside around the inflation and urine tubes.

6. The method of claim 5 and the step of providing an anchoring means on said urine tube and inflation tube at the outlet end of the urethra for maintaining the lower end portion of the balloon in the urethra.

7. The method of claim 6 and the further steps of positioning the anchoring means in operative engagement with the body at the outlet end of the urethra and pulling the balloon tight for seating the lower end portion in the neck of the urethra.

8. The method of claim 7 and the step of providing a support shell around the penis and extending the outlet end of the urine tube outwardly of the outer end of the support shell with the anchoring means being in engagement with the outer end of the support shell and the inner end of the support shell engaging the users body adjacent the penis to provide resistance in pulling the balloon tight.

9. The method of claim 5 wherein the step of providing a urine tube further includes the step of providing a flexible, longitudinally collapsible urine tube such that longitudinal compressive pressure applied to said urine tube will not unseat said balloon lower portion in the urethra at the neck and orifice of the bladder and cause leakage on the outside around the inflation and urine tubes.

10. The method of claim 9 wherein the step of providing a flexible longitudinally collapsible urine tube further includes the step of providing a urine tube of elastomer silicone material.

11. The method of claim 10 wherein the step of positioning the anchoring means in operative engagement with the body at the outlet end of the urethra further includes the step of providing a collar anchoring means on the urine and air tubes operatively engaging the pubic bone thereby limiting longitudinal movement of said tubes into said bladder.

12. The method of claim 5 wherein the step of providing an inflation tube having an inflatable balloon at one end further includes the step of providing a balloon of less than 40 cc.

13. The method of controlling the urine flow in the urethra comprising the steps of, providing an inflation tube having an inflatable balloon at one end and an inlet at the opposite end, said balloon when inflated having an enlarged, upper portion and a downwardly extending reduced in size lower end portion, providing a urine tube having inlet and outlet ends operatively associated with the inflation tube with the urine tube extending through the balloon, inserting the urine tube, inflation tube and balloon into the urethra and positioning the deflated balloon in the bladder with the lower end portion at the urethra at the neck and orifice of the bladder with the inlet end of the urine tube being in the bladder, inflating the balloon, and seating the lower end portion of the balloon in the urethra at the neck and orifice of the bladder without changing the shape of the balloon upon being seated, whereby the upper portion retains the balloon in the bladder and the lower end portion functions as a plug seal in the urethra at the neck and orifice of the bladder to prevent urine flow in the urethra on the outside around the inflation and urine tubes.

14. The method of controlling the urine flow in the urethra comprising the steps of:

providing a tube having inflation and urine lumens and said inflation lumen having an inflatable balloon at one end and an inlet at the opposite end, said balloon when inflated having an enlarged, upper portion and a downwardly extending reduced in size lower end portion, inserting the tube and balloon into the urethra and positioning the deflated balloon in the bladder with the lower end portion in the urethra at the neck and orifice of the bladder with the inlet end of the urine lumen being in the bladder, inflating the balloon, and seating the lower end portion of the balloon in the urethra at the neck and orifice of the bladder without changing the shape of the balloon, whereby the upper portion retains the balloon in the bladder and the lower end portion functions as a plug seal in the urethra at the neck and orifice of the bladder to prevent urine flow in the urethra on the outside around the tube.

* * * * *